United States Patent [19]

Trivedi

[11] Patent Number: 5,030,653

[45] Date of Patent: Jul. 9, 1991

[54] ANTIHYPERLIPIDEMIC AND ANTIATHEROSCLEROTIC COMPOUNDS AND COMPOSITIONS

[75] Inventor: Bharat K. Trivedi, Canton, Mich.

[73] Assignee: Warner-Lambert Company, Morris Plains, N.J.

[21] Appl. No.: 602,015

[22] Filed: Oct. 23, 1990

Related U.S. Application Data

[62] Division of Ser. No. 478,296, Feb. 9, 1990, Pat. No. 4,999,373, which is a division of Ser. No. 364,349, Jun. 9, 1989, Pat. No. 4,948,806, which is a division of Ser. No. 176,080, Mar. 30, 1988, Pat. No. 4,868,210.

[51] Int. Cl.$^5$ .................. C07C 275/28; A61K 31/235; A61K 31/19; A61K 31/17

[52] U.S. Cl. .................................. 514/510; 514/539; 514/542; 514/562; 514/563; 514/564; 514/586; 514/587; 514/595; 514/596; 514/598; 514/824; 560/10; 560/16; 560/34; 562/427; 562/428; 562/439; 564/26; 564/27; 564/28; 564/29; 564/44; 564/48; 564/52

[58] Field of Search .............. 564/28, 48, 52; 560/10, 560/34; 562/427, 439; 514/510, 562, 564, 586, 587, 596, 598

[56] References Cited

U.S. PATENT DOCUMENTS

| | | | |
|---|---|---|---|
| 3,555,086 | 1/1971 | Weis et al. | 564/48 |
| 4,868,210 | 9/1989 | Trivedi | 560/10 |
| 4,981,865 | 1/1991 | Belliotti et al. | 514/510 |

FOREIGN PATENT DOCUMENTS

| | | | |
|---|---|---|---|
| 0335374 | 10/1989 | European Pat. Off. | 564/52 |
| 0935187 | 8/1963 | United Kingdom | 564/28 |

OTHER PUBLICATIONS

Erden, F. et al., "Acyl Enamines, etc.", CA 75, 151493n, 1971.

*Primary Examiner*—Glennon H. Hollrah
*Attorney, Agent, or Firm*—Ruth H. Newtson

[57] ABSTRACT

Certain N-2,6-dialkyl- or N-2,6-dialkoxyphenyl-N'-arylalkylurea compounds are potent inhibitors of the enzyme acyl CoA:cholesterol acyltransferase (ACAT), and are thus useful agents for the treatment of hypercholesterolemia or atherosclerosis.

4 Claims, No Drawings ns
ANTIHYPERLIPIDEMIC AND ANTIATHEROSCLEROTIC COMPOUNDS AND COMPOSITIONS

This application is a divisional of U.S. Ser. No. 478,296 filed Feb. 9, 1990 now U.S. Pat. No. 4,999,373, which is a divisional of U.S. Ser. No. 364,349 filed June 9, 1989 now U.S. Pat. No. 4,948,806 which is a divisional of U.S. Ser. No. 176,080 filed Mar. 30, 1988, and issued as U.S. Pat. No. 4,868,210 on Sept. 19, 1989.

BACKGROUND OF THE INVENTION

This invention relates to chemical compounds having pharmacological activity, to pharmaceutical compositions which include these compounds, and to a pharmaceutical method of treatment. More particularly, this invention concerns certain substituted urea and thiourea compounds which inhibit the enzyme acyl-coenzyme A:cholesterol acyltransferase (ACAT), pharaceutical compositions containing these compounds, and a method of treating hypercholesterolemia and atherosclerosis.

In recent years the role which elevated blood plasma levels of cholesterol plays in pathological conditions in man has received much attention. Deposits of cholesterol in the vascular system have been indicated as causative of a variety of pathological conditions including coronary heart disease.

Initially, studies of this problem were directed toward finding therapeutic agents which would be effective in lowering total serum cholesterol levels. It is now known that cholesterol is transported in the blood in the form of complex particles consisting of a core of cholesteryl esters plus triglycerides and an exterior consisting of primarily of phospholoipis and a variety of types of protein which are recognized by specific receptors. For example, cholesterol is carried to the sites of deposit in the blood vessels in the form of low density lipoprotein cholesterol (LDL cholesterol) and away from such sites of deposit by high density lipoprotein cholesterol (HDL cholesterol).

Following these discoveries, the search for therapeutic agents which control serum cholesterol turned to finding compounds which are more selective in their action; that is, agents which are effective in elevating the blood serum levels of HDL cholesterol and/or lowering the levels of LDL cholesterol. While such agents are effective in moderating the levels of serum cholesterol, they have little or no effect on controlling the initial absorption of dietary cholesterol in the body through the intestinal wall.

In intestinal mucosal cells, dietary cholesterol is absorbed as free cholesterol which must be esterified by the action of the enzyme acyl-CoA: cholesterol acyltransferase (ACAT) before it can be packaged into the chylomicrons which are then released into the blood stream. Thus, therapeutic agents which effectively inhibit the action of ACAT prevent the intestinal absorption of dietary cholesterol into the blood stream or the readsporption of cholesterol which has been previously released into the intestine through the body's own regulatory action.

U.S. Pat. No. 4,387,105 to DeVries, et al. discloses a method of treating atherosclerosis employing certain dialkylurea and dialkylthiourea compounds.

U.S. Pat. No. 4,387,106 to DeVries, et al. discloses a method of treating aterosclerosis using certain N-phenyl- or N-[substituted (phenyl)]-N',N'-dialkylurea and thiourea compounds.

U.S. Pat. No. 4,387,106 to DeVries, et al. discloses certain methods for treating atherosclerosis using certain trisubstituted N-[substituted(phenyl)]-N',N'-diarylalkyl urea and thiourea compounds.

U.S. Pat. No. 4,397,868 to DeVries, et al. discloses method for treating atherosclerosis using certain trisubstituted urea compounds.

U.S. Pat. No. 4,473,579 to DeVries, et al. discloses certain tetrasubstituted urea compounds and their use as agents for treating atherosclerosis.

SUMMARY OF THE INVENTION

The present invention provides a class of compounds with ACAT inhibitory activity having the structure

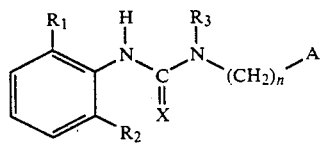

wherein
$R_1$ and $R_2$ are independently selected from alkyl or alkoxy of from one to six carbon atoms. The atom X is oxygen or sulfur, and n is zero, one or two.
$R_3$ is hydrogen, alkyl of from one to seven carbon atoms or phenylmethyl.

The group A is selected from

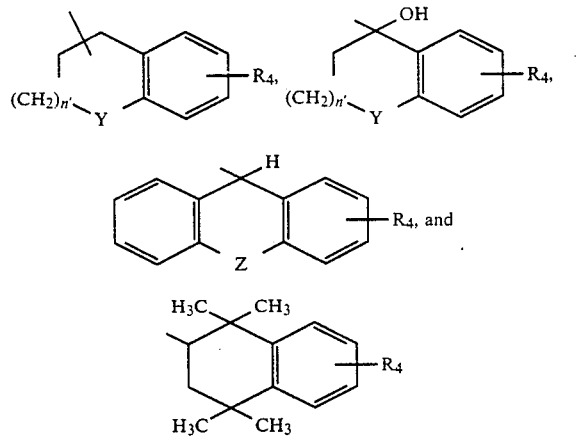

where n' is one or two, Y is a direct bond, $>CH_2$, $>O$, or $>S$, and Z is a direct bond, $>CH_2$, $-CH=CH-$, $-CH_2CH_2-$, $>O$, or $>S$.

$R_4$ is selected from alkyl of from one to six carbon atoms, hydroxy, acetoxy, alkoxy of from one to six carbon atoms, phenoxy, fluorine, chlorine, bromine, nitro, trifluoromethyl, carboxyl, $-COO$-alkyl in which the alkyl portion contains from one to four carbon atoms, amino, alkylamino of from one to six carbon atoms, dialkylamino in which the alkyl groups independently contain from one to six carbon atoms, or $-NH$-acetyl.

DETAILED DESCRIPTION

The compounds of the present invention form a class of substituted ureas and thioureas having potent activity as inhibitors of the enzyme acyl CoA: cholesterol acyltransferase (ACAT).

In the compounds of the present invention, the first nitrogen atom of the urea or thiourea moiety is monosubstituted by a phenyl ring which is substituted in the 2- and 6-positions by groups selected from alkyl or alkoxy of from one to six carbon atoms. It is believed that this substitution pattern is important in determining the activity of the compounds of this invention as inhibitors of the ACAT enzyme. Preferred compounds of this invention are those in which $R_1$ and $R_2$ are alkyl, preferably 1-methylethyl.

In preferred compounds of this invention, the second nitrogen atom of the urea or thiourea moiety is monosubstituted with a polycyclic group which may be either directly attached to the second nitrogen, or may be attached through an alkylene linkage of one or two carbon atoms, i.e., —$CH_2$— or —$CH_2CH_2$—. Alternatively, the second nitrogen atom of the urea or thiourea moiety is disubstituted by straight or branched alkyl of from one to seven carbon atoms or phenylmethyl and a polycyclic group.

The polycyclic group is selected from 2,3-dihydro-1H-inden-1-yl; 2,3-dihydro-1H-inden-2-yl; 2,3-dihydro-1-hydroxy-1-indenyl; 2,3-dihydrobenzofuran-2-yl; 2,3-dihydrobenzofuran-3-yl; 2,3-dihydrobenzo[b]-thiophen-2-yl; 2,3-dihydrobenzob]thiophen-3-yl; 1,2,3,4-tetrahydronaphth-1-yl; 1,2,3,4-tetrahydronaph-2-yl; 1,2,3,4-tetrahydro-1-hydroxy-1-naphthyl; 3,4-dihydro-(2H)1-benzopyran-3-yl; 3,4-dihydro-(2H)1-benzopyran-4-yl; 3,4-dihydro-(2H)1-benzothiopyran-3-yl; 3,4-dihydro-(2H)1-benzothiopyran-4-yl; 6,7,8,9-tetrahydro-5H-benzocycloheptan-8-yl; 6,7,8,9-tetrahydro-5H-benzocycloheptan-9-yl; 2,3,4,5-tetrahydro-1-benzoxepin-4-yl; 2,3,4,5-tetrahydro-1-benzoxepin-5-yl; 2,3,4,5-tetrahydro-1-benzothiepin-4-yl; and 2,3,4,5-tetrahydro-1-benzothiepin-5-yl; 9-fluorenyl; 9-xanthenyl; 9-thioxanthenyl; 10,11-dibenzo[a,d]cycohepten-5-yl and 1,2,3,4-tetrahydro-1,1,4,4-tetramethylnaphthen-2-yl.

The various polycyclic systems enumerated above may be unsubstituted or may be substituted by alkyl of from one to six carbon atoms, hydroxy, acetoxy, alkoxy of from one to six carbon atoms, phenoxy, fluorine, chlorine, bromine, nitro, trifluoromethyl, carboxyl, —COO-alkyl in which the alkyl portion contains from one to four carbon atoms, amino, alkylamino of from one to six carbon atoms, dialkylamino in which the alkyl groups independently contain from one to six carbon atoms, or —NH-acetyl.

Specific examples of compounds contemplated as falling within the scope of the invention are the following:

N-[2,6-bis(1-Methylethyl)phenyl]-N'-(9H-fluoren-9-ylmethyl)urea.

N-[2,6-bis(1-Methylethyl)phenyl]-N'-(9H-xanthen-9-ylmethyl)urea.

N-[2,6-bis(1-Methylethyl)phenyl]-N'-[(2,3dihydro-1H-inden-1-yl)methyl]urea.

N-[2,6-bis(1-Methylethyl)phenyl]-N'-1,2,3,4-tetrahydro-2-naphthalenyl)urea.

N-[2,6-bis(1-Methylethyl)phenyl]-N'-[(1,2,3,4-tetrahydro-1-naphthalenyl)methyl]urea.

N-[2,6-bis(1-Methylethyl)phenyl]-N'-[(3,4-dihydro-1-naphthalenyl)methyl]urea.

N-[2,6-bis(1-Methylethyl)phenyl]-N'-[(2,3-dihydro-1-hydroxy-1H-inden-1-yl)methyl]urea.

N-[2,6-bis(1-Methylethyl)phenyl]-N'-[(1,2,3,4tetrahydro-1-hydroxy-1-naphthalenyl)methyl]urea.

N-[2,6-bis(1-Methylethyl)phenyl]-N'-2,3,4,5-tetrahydro-1-benzoxepin-4-yl)urea.

N-[2,6-bis(1-Methylethyl)phenyl]-N'-(3,4-dihydro-2H-1-benzopyran-3-yl)urea.

N-(2,6-Dimethylphenyl)-N'-(1,2,3,4-tetra-hydro-1,1,4,4-tetramethyl-2-naphthalenyl)urea.

N-[2,6-bis(1-Methylethyl)phenyl]-n-(1,2,3,4-tetrahydro-1,1,4,4-tetramethyl-2-naphthalenyl)-urea.

N-[2,6-bis(1-Methylethyl)phenyl]-N'-[(1,2,3,4-tetrahydro-7-methoxy-2-naphthalenyl)methyl]urea.

N'-[2,6-bis(1-Methylethyl)phenyl]-N-(3,4-dihydro-2H-1-benzopyran-3-yl)-N-(1-methylethyl)urea.

By the term "alkyl" as used throughout this specification and the appended claims is meant a branched or unbranched hydrocarbon grouping derived from a saturated hydrocarbon of from one to six carbon atoms by removal of a single hydrogen atom. Examples of alkyl groups contemplated as falling within the scope of this invention include methyl, ethyl, propyl, 1-methylethyl, butyl, 1-methylpropyl, 2-methylpropyl, and 1,1-dimethylethyl.

By the term "alkoxy" is meant an alkyl group, as defined above, attached to the parent molecular moiety through an oxygen atom.

The compounds of this invention may exist in different enantiomorphic forms due to the presence of one or more asymmetric centers in the molecule. This invention contemplates all enantiomorphic forms of the compounds as well as mixtures thereof including racemic mixtures. Individual enantiomers may be obtained, if desired, by resolution techniques known to the art as, for example, formation of diastereomers and fractional recrystallization or resolution on chiral chromatographic columns.

In those instances where the compounds of the present invention bear a basic nitrogen atom as, for example, when the polycyclic moiety is substituted by amino, alkylamino, or dialkylamino, the compounds are capable of forming acid addition salts. These acid addition salts are also contemplated as falling within the scope of this invention.

The acid addition salts may be generated from the free base forms of the compounds by reaction of the latter with one equivalent of a suitable nontoxic, pharmaceutically acceptable acid, followed by evaporation of the solvent employed for the reaction and recrystallization of the salt, if required. The free base may be recovered from the acid addition salt by reaction of a water solution of the salt with a suitable base such as sodium carbonate, sodium bicarbonate, potassium carbonate, sodium hydroxide, and the like.

Suitable acids for forming acid addition salts of the compounds of this invention include, but are not necessarily limited to acetic, benzoic, benzenesulfonic, tartaric, hydrobromic, hydrochloric, citric, fumaric, gluconic, glucuronic, glutamic, lactic, malic, maleic, methanesulfonic, pamoic, salicylic, stearic, succinic, sulfuric, and tartaric acids.

In those cases where the compounds of the present invention bear an acidic functional group, as for example when the polycyclic moiety is substituted by carboxyl, the compounds are capable of forming base addition salts with pharmaceutically acceptable metal cations and bases. Suitable metals are aluminum, calcium, lithium, magnesium, potassium, sodium, and zinc. Suitable bases are ammonia, and organic amines which are sufficiently strong bases to form salts with the carboxyl group.

The metal salts and base addition salts may be generated from the free acid form of the compounds by reaction of the latter with one equivalent of a suitable nontoxic, pharmaceutically acceptable metal hydroxide, carbonate, or bicarbonate, followed by evaporation of the solvent employed for the reaction and recrystallization of the salt, if required. The free acid may be recovered from the metallic salt or base addition salt by reaction of a water solution of the salt with a suitable acid such as dilute aqueous hydrochloric acid.

The class of metals, acids, and organic amine bases suitable for the formation of nontoxic, pharmaceutically acceptable salts of the compounds of this invention is well known to practitioners of the pharmaceutical formulation arts. (See, for example, Stephen N. Berge, et al. J. Pharm. Sciences, 66:1–19 (1977)).

While the salts may vary from the free base or free acid forms of the compounds of this invention in certain properties such as melting point and solubility, they are considered equivalent for the purposes of this invention.

Further, the compounds of this invention may exist in unsolvated as well as solvated forms with pharmaceutically acceptable solvents such as water, ethanol and the like. In general, the solvated forms are considered equivalent to the unsolvated forms for the purposes of this invention.

The compounds of the present invention are prepared by reacting the appropriately substituted 2,6-(disubstituted)phenyl isocyanate or thioisocyanate compound with the desired polycyclic amine to obtain the substituted urea or thiourea compounds of the present invention.

The reaction is generally carried out in a polar aprotic organic solvent such as ethyl acetate, at any temperature between room temperature and the boiling point of the solvent, with room temperature being preferred.

The reaction is allowed to proceed until analysis of the mixture by a means such as chromatography indicates that the reaction is substantially complete. Reaction times may vary between about two hours to about 24 hours, depending upon the particular reagents and reaction temperature employed.

The polycyclic amine starting compounds are prepared by the general methods detailed in Reaction Schemes I–IV. Referring to Reaction Scheme I, the known or commercially available ketones, chromanones (where X=O), or thiochromanones (where X=S), 2, are converted to the corresponding oximes by reaction with hydroxylamine hydrochloride in the usual manner. In a second step, the intermediate hydroxylamines are tosylated by reaction with p-toluenesulfonyl chloride in ridine to produce the oxime tosylates, 3.

REACTION SEQUENCE I

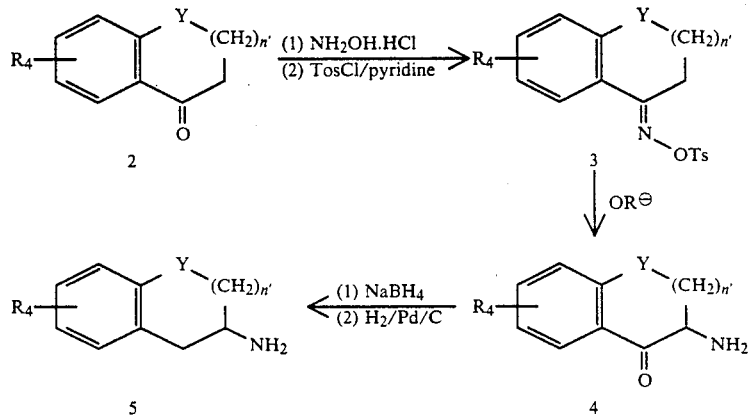

The hydroxylamine toxylates, 3, are next converted to the α-aminoketones, 4, by treating 3 with base such alkoxide ion (the so-called "Neber rearrangement." See C. O'Brien, Chem. Rev., 64: 81 (1964)). The aminoketones, 4, are then reduced by the action of sodium borohydride to the intermediate alcohols which are then further reduced by the action of hydrogen over palladium on charcoal to the amine compounds, 5. The amines, 5, are coupled with the desired 2,6-disubstituted isocyanate or thioisocyanate compound to produce compounds of the present invention.

Referring to Reaction Scheme II, the polycyclic amine starting compounds useful for preparing the compounds of this invention are prepared by an alternative method in which the bicyclic ketone, 2, is reacted with trimethylsilyl cyanide (Aldrich Chemical Co., Milwaukee, Wis., USA) in the presence of a Lewis acid catalyst to produce the trimethylsilyl derivative of the corresponding cyanohydrin, 6. The details of this reaction are discussed in Chem. Commun., 55: 2 (1973) and Tetrahedron Lett., 3773 (1978).

The trimethylsilyl cyanohydrin, 6, is next reduced to the corresponding hydroxylamine by the action of lithium aluminum hydride to the corresponding hydroxylamine, 7. This compound may be coupled directly with the desired 2,6-(disubstituted)phenyl isocyanate or thioisocyante to produce compounds of the present invention or, alternatively, may be dehydrated to the corresponding alkenamine, 8, by the action of acid. The alkenamine, 8, is reduced to the saturated amine, 9, by hydrogen over Raney-nickel in acetic acid. This overall conversion is discussed in D. Evans, et al., J. Org. Chem., 39: 917 (1974). The amine is then coupled with the desired 2,6-(disubstituted)phenyl isocyanate or thioisocyanate to produce compounds of the present invention.

REACTION SEQUENCE II

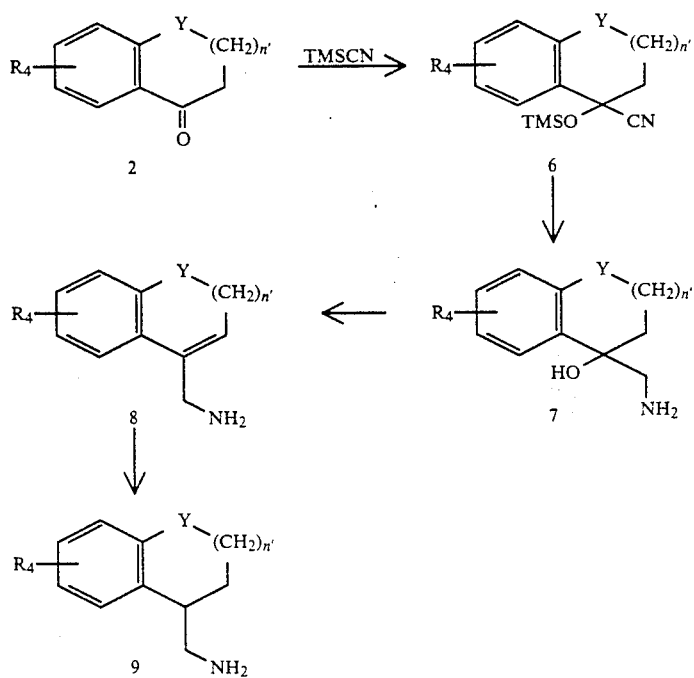

Referring to Reaction Sequence III, an alternative method for preparing starting materials for compounds of the present invention is shown.

The known or commercially available acids, 10, are converted by the action of oxalyl chloride and ammonium hydroxide into the corresponding amides, 11. The amides, 11, are next reduced by the action of lithium aluminum hydride to the methylamines, 12, which are then coupled with the desired 2,6-(disubstituted)phenyl isocyanates or thioisocyanates to produce the compounds of this invention.

Alternatively, the ketones, 13, are converted under Wittig Reaction conditions to the corresponding cyano compounds 14. Compound 14 is reduced by the action of hydrogen over palladium on charcoal to produce the amines, 15, which are then coupled with the desired 2,6-(disubstituted)phenyl isocyanates or thioisocyanates to produce the compounds of this invention.

Referring to Reaction Sequence IV, the substituted bicyclic methylamine starting compounds may be synthesized by an alternative method using a procedure adapted from R. C. Gupta, et al. *Indian J. Chem. Section B,* 1982, 21B, 334. The commercially available or known substituted salicaldehydes, 16, are reacted with acrylonitrile to produce the substituted bicyclic compounds, 17. These compounds are subsequently reduced by the action of hydrogen over palladium on charcoal to the saturated amines, 18, which are subsequently reacted with the desired 2,6-(disubstituted)phenyl isocyanate or thioisocyanate to produce the compounds of this invention.

REACTION SEQUENCE III

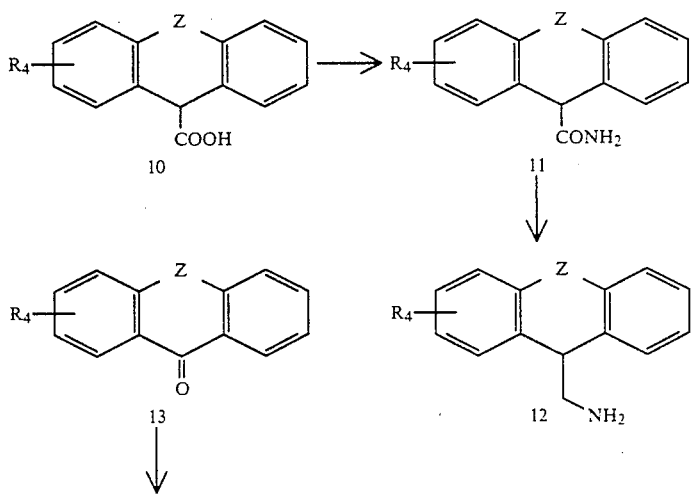

REACTION SEQUENCE III

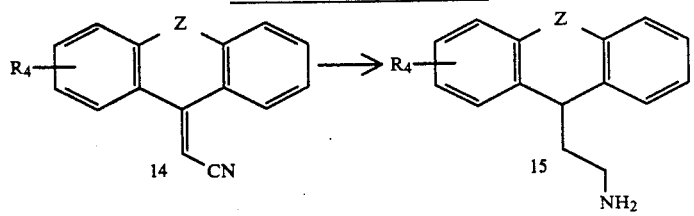

REACTION SEQUENCE IV

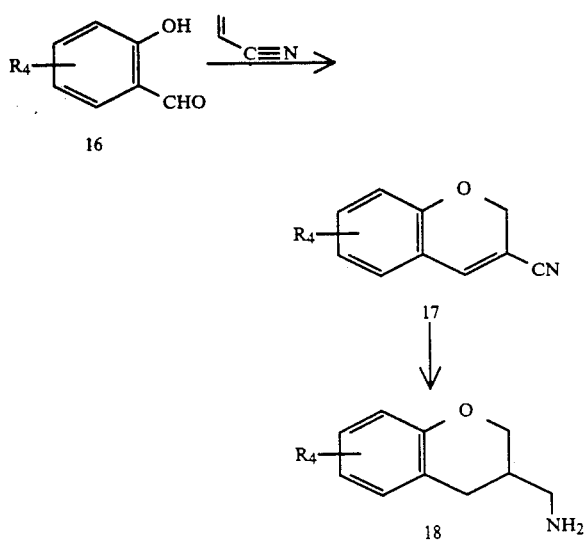

As shown by the data presented below in Table 1, the compounds of the present invention are potent inhibitors of the enzyme acyl-CoA:cholesterol acyl-transferase (ACAT), and are thus effective in inhibiting the esterification and transport of cholesterol across the intestinal cell wall. The compounds of the present invention are thus useful in pharmaceutical formulations for the treatment of hypercholesterolemia or atherosclerosis.

In Vitro Tests

The ability of representative compounds of the present invention to inhibit ACAT was measured using an in vitro test more fully described in Field, F. J. and Salone, R. G., *Biochemica et Biophysica* 712: 557-570 (1982). The test assesses the ability of a test compound to inhibit the acylation of cholesterol by oleic acid by measuring the amount of radiolabeled cholesterol oleate formed from radiolabeled oleic acid in a tissue preparation containing rabbit intestinal microsomes.

The data appear in Table 1 where they are expressed as $IC_{50}$ values; i.e. the concentration of test compound required to inhibit 50% expression of the enzyme.

In therapeutic use as agents for treating hypercholesterolemia or atherosclerosis, the compounds utilized in the pharmaceutical method of this invention are administered to the patient at dosage levels of from 50 to 1000 mg per day. For a normal human adult of approximately 70 kg of body weight, this translates into a dosage of from 5 to 20 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

TABLE 1

| Compound of Example | $IC_{50}$ $\mu M$ |
|---|---|
| 1 | 0.027 |
| 2 | 0.042 |
| 3 | 0.027 |
| 4 | 0.036 |
| 5 | 0.029 |
| 6 | 0.81 |
| 7 | 0.35 |
| 8 | 0.052 |
| 9 | 0.041 |
| 10 | 0.10 |
| 11 | 0.084 |
| 12 | 0.27 |
| 13 | 0.089 |

For preparing pharmaceutical compositions from the compounds of this invention, inert, pharmaceutically acceptable carriers can be either solid or liquid. Solid form preparations include powders, tablets, dispersible granules, capsules, and cachets.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

Powders and tablets preferably contain between about 5 to about 70% by weight of the active ingredient. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner, cachets are also included.

Tablets, powders, cachets, and capsules can be used as solid dosage forms suitable for oral administration.

Liquid form preparations include solutions suitable for oral administration, or suspensions and emulsions suitable for oral administration. Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

The following examples are provided to enable one skill in the art to practice the present invention, but are not to be read as limiting the scope of the invention as it is defined by the appended claims.

EXAMPLE 1

Preparation of N-[2,6-bis(1-methylethyl)phenyl]-N'-(9H-fluoren-9-ylmethyl)urea

To 3.88 g (0.02 mol of 9-fluorenemethyl amine in 100 ml of ethyl acetate was added, in one portion, 4.06 g (0.02 mol) of 2,6-diisopropylphenyl isocyanate in 100 ml of ethyl acetate.

The resulting mixture was stirred at room temperature for twenty hours, after which time the white solid precipitate which formed was collected by filtration, washed with hexane, and dried to yield 4.3 g of N-2,6-bis(1-methylethyl)phenyl ]-N'-(9H-fluoren-9-ylmethyl-)urea, mp 217°–218° C.

Analysis for: $C_{28}H_{34}N_2O \cdot \frac{1}{4}H_2O$: Calc.: C, 80.46%; H, 7.62%; N, 6.95%; Found: C, 80.56%; H, 7.53%; N, 6.91%.

EXAMPLE 2

Preparation of N-[2,6-bis(1-methylethyl)phenyl]-N'-9H-xanthen-9-ylmethyl)urea

Using the method of Example 1, but starting with 4.3 g (0.02 mol) of 9-xanthenemethyl amine, there was obtained 5.3 g of N-[2,6-bis(1-methyl-ethyl)phenyl]-N'-9H-xanthen-9-ylmethyl)urea, mp 250°–251° C.

Analysis for: $C_{27}H_{30}N_2O_2$: Calc.: C, 78.23%; H, 7.29%; N, 6.76%; Found: C, 77.94%; H, 7.20%; N, 6.67%.

EXAMPLE 3

Preparation of N-[2,6-bis(1-methylethyl)phenyl]-N'-[(2,3-dihydro-1H-inden-1-yl)methyl]urea Using the method of Example 1, but starting with 1.47 g (0.01 mol) of 1-indanylmethyl amine, there was obtained 2.9 g of N-[2,6-bis(1-methylethyl)phenyl]-N'-[(2,3-dihydro-1H-inden-1-yl)methyl]urea, mp 183°–185° C.

Analysis for: $C_{23}H_{30}N_2O$: Calc.: C, 78.82%; H, 8.63%; N, 7.99%; Found: C, 78.69%; H, 8.66%; N, 7.95%.

EXAMPLE 4

Preparation of N-[2,6-bis(1-methylethyl)phenyl]-N'-[(1,2,3,4-tetrahydro-1-naphthalenyl)methyl)urea Using the method of Example 1, but starting with 3.23 g (0.02 mol) of 1,2,3,4-tetrahydronaphthalenyl-1-methylamine, there was obtained 6.8 g of N-[2,6-bis(1-methylethyl)phenyl]-N'-[(1,2,3,4-tetrahydro-1-naphthalenyl)methyl)urea, mp 189°–190° C.

Analysis for: $C_{13}H_{32}N_2O$: Calc.: C, 79.08%; H, 8.85%; N, 7.68%; Found: C, 79.08%; H, 8.88%; N, 7.59%.

EXAMPLE 5

Preparation of N-[2,6-bis(1-methylethyl)phenyl]-N'-[(3,4-dihydro-1-naphthalenyl)methyl]urea Using the method of Example 1 but starting with 3.18 g of 3,4-dihydro-1-naphthalenylmethyl amine, there was obtained 2.6 g of N2,6-bis(1-methylethyl)phenyl]-N'-[(3,4-dihydro-1-naphthalenyl)methyl]urea, mp 170°–171° C.

Analysis for: $C_{24}H_{30}N_2O$: Calc.: C, 79.51%; H, 8.34%; N, 7.72%; Found: C, 79.61%; H, 8.48%; N, 7.59%.

EXAMPLE 6

Preparation of N-[2,6-bis(1-methylethyl)phenyl]-N'-[(2,3-dihydro-1-hydroxy-1H-inden-1-yl)methyl]-urea Using the method of Example 1 but starting with 3.26 g of 2,3-dihydro-1-hydroxy-1H-inden-1-ylmethylamine, there was obtained 5.0 g of N-[2,6-bis(1-methylethyl)-phenyl]-N'-[(2,3-dihydro-1-hydroxy-1H-inden-1-yl)methyl]urea, mp 173°–174° C.

Analysis for: $C_{23}H_{30}N_2O_2$: Calc.: C, 75.37%; H, 8.25%; N, 7.64%; Found: C, 74.97%; H, 8.14%; N, 7.44%.

EXAMPLE 7

Preparation of N-[2,6-bis(1-methylethyl)phenyl]-N-[(1,2,3,4-tetrahydro-1-hydroxy-1-naphthalenyl)methyl]urea Using the method of Example 1 but starting with 3.23 g of 1,2,3,4-tetrahydro-1-hydroxy-1-naphthalenylmethyl amine, there was obtained 3.8 g of N-[2,6-bis-(1-methylethyl)phenyl]-N'-[(1,2,3,4-tetrahydro-1-hydroxy-1-naphthalenyl)methyl]urea, mp 170°–171° C.

Analysis for: $C_{24}H_{32}N_2O_2$: Calc. C, 75.75%; H, 8.48%; N, 7.36%; Found: C, 75.71%; H, 8.48%; N, 7.29%.

EXAMPLE 8

Preparation of N-[2,6-bis(1-methylethyl)phenyl]-N'-(2,3,4,5-tetrahydrobenzoxepin-4-yl)urea To a solution of 2,3,4,5-tetrahydro-benzoxepin-4-amine (0.95 g, 5.8 mmol) in 50 ml of ethyl acetate was added 1.18 g (5.8 mmol) of 2,6-bis(1-methylethyl)phenyl isocyanate. The resulting mixture was stirred at room temperature for 20 hours. The precipitated solid was collected by filtration, washed with ethyl acetate, and dried to yield 1.1 g of N-[2,6-bis(1-methylethyl)phenyl] -N'-(2,3,4,5-tetrahydrobenzoxepin-4-yl)urea, mp 184°–186° C.

EXAMPLE 9

Preparation of
N-[2,6-bis(1-methylethyl)phenyl]-N'-(1,2,3,4-tetrahydro-2-naphthalenyl)urea Using the method of Example 1, but starting with 1,2,3,4-tetrahydro-2-naphthylamine, there was obtained N-[2,6-bis(1-methylethyl)phenyl]-N'-(1,2,3,4-tetrahydro-2-naphthalenyl)urea, mp 214°–215° C.

Analysis for: $C_{23}H_{30}N_2O$: Calc.: C, 78.81%; H, 8.62%; N, 7.99%; Found: C, 78.82%; H, 8.77%; N, 8.06%.

EXAMPLE 10

Preparation of
N-[2,6-bis(1-methylethyl)phenyl]-N'-(3,4-dihydro-2H-1-benzopyran-3-yl)urea To a solution of 3,4-dihydro-3-amino-2H-benzopyran (0.9 g, 6 mmole) in 50 ml of ethyl acetate, there was added 1.22 g (6 mmol) of 2,6-bis(1-methylethyl)phenyl isocyanate. The resulting mixture was stirred at room temperature for twenty hours. The solvent was removed under vacuum and the residue was suspended in 20% ethyl acetate/hexane. The precipitated solid was collected by filtration and dried to yield 1.25 g of N-[2,6-bis-(1-methylethyl)phenyl]-N'-(3,4-dihydro-2H-1-benzopyran-3-yl)urea, mp 186°–188° C.

Analysis for: $C_{22}H_{28}N_2O_2$: Calc.: C, 74.97%; H, 8.00%; N, 7.94%; Found: C, 74.71%; H, 7.89%; N, 7.87%.

EXAMPLE 11

Preparation of
N-[2,6-bis(1-methylethyl)phenyl]-N'-[(1,2,3,4-tetrahydro-7-methoxy-2-naphthalenyl)methyl]urea Using the method of Example 1, but starting with 1,2,3,4-tetrahydro-7-methoxy-2-naphthylamine, there was obtained N-[2,6-bis(1-methylethyl)phenyl]-N'-[(1,2,3,4-tetrahydro-7-methoxy-2-naphthalenyl)methyl]urea, mp 171°–172° C.

Analysis for: $C_{25}H_{34}N_2O_2$: Calc.: C, 76.10%; H, 8.68%; N, 7.09%; Found: C, 75.89%; H, 8.78%; N, 7.02%.

EXAMPLE 12

Preparation of
N-(2,6-dimethylphenyl)-N'-(1,2,3,4-tetrahydro-1,1,4,4-tetramethyl-2-naphthalenyl)urea Using the method of Example 1, but starting with 2,6-dimethylphenyl isocyanate and 1,2,3,4-tetrahydro-1,1,4,4-tetramethyl-2-naphthylamine, there was obtained N-(2,6-dimethylphenyl)-N'-(1,2,3,4-tetrahydro-1,1,4,4-tetramethyl-2-naphthalenyl)urea, mp 216°–218° C.

Analysis for: $C_{23}H_{30}N_2O$: Calc.: C, 78.81%; H, 8.62%; N, 7.99%; Found: C, 78.60%; H, 8.61%; N, 7.88%.

EXAMPLE 13

Preparation of
N-[2,6-bis(1-methylethyl)phenyl]-N'-(1,2,3,4-tetrahydro-1,1,4,4-tetramethyl-2-naphthalenyl)urea Using the method of Example 12, but starting with 2,6-bis(1-methylethyl)phenyl isocyanate, there was obtained N-[2,6-bis(1-methylethyl)phenyl]-N'-(1,2,3,4-tetrahydro-1,1,4,4-tetramethyl-2-naphthalenyl)urea, mp 180°–181° C.

Analysis for: $C_{27}H_{38}N_2O$: Calc.: C, 79.75%; H, 9.41%; N, 6.88%; Found: C, 80.13%; H, 9.52%; N, 6.67%.

EXAMPLE 14

Preparation of
N'-[2,6-bis(1-methylethyl)phenyl]-N-(3,4-dihydro-2H-1-benzopyran-3-yl)-N-(1-methylethyl)urea Using the method of Example 1, but starting with N-(1-methylethyl)-3,4-dihydro-2H-1-benzo-pyran-3-ylamine, there was obtained N'-[2,6-bis-(1-methylethyl)phenyl]-N-(3,4-dihydro-2H-1-benzo- pyran-3-yl)-N-(1-methylethyl)urea, mp 169°–172° C.

Analysis for: $C_{25}H_{34}N_2O_2$: Calc.: C, 76.10%; H, 8.69%; N, 7.10%; Found: C, 76.24%; H, 8.72%; N, 7.03%.

I claim:

1. A compound having the formula

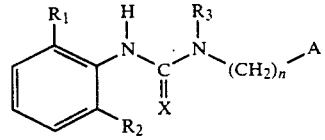

wherein
$R_1$ and $R_2$ are independently selected from alkyl or alkoxy of from one to six carbon atoms;
$R_3$ is hydrogen, alkyl of from one to seven carbon atoms, or phenylmethyl;
X is oxygen or sulfur;
n is zero, one or two;
A is selected from

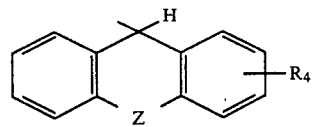

Z is
a direct bond,
$>CH_2$,
—CH=CH—
—$CH_2CH_2$—,
$R_4$ is selected from
hydrogen
alkyl of from one to six carbon atoms,
hydroxy,
acetoxy,
alkoxy of from one to six carbon atoms,
phenoxy,
fluorine,
chlorine,
bromine,
nitro, trifluoromethyl,
carboxyl,
—COO-alkyl in which the alkyl portion contains from one to four carbon atoms,
amino,
alkylamino of from one to six carbon atoms,
dialkylamino in which the alkyl groups contain from one to six carbon atoms,
—NH-acetyl; or a pharmaceutically acceptable salt thereof.

2. A compound as defined by claim 1 having the same N-[2,6-bis(1-methylethyl)phenyl]-N-40 -(9H-fluoren-9-ylmethyl)urea.

3. A pharmaceutical composition for treating hyperchlesterolemia or atherosclerosis comprising an ACAT-inhibitory effective amount of a compound as defined by claim 1 in combination with a pharmaceutically acceptable carrier.

4. A method of treating hypercholesterolemia or athersclerosis comprising administering to a mammal in need of such treatment an ACAT-inhibitory effective amount of a compound as defined by claim 1.

* * * * *